(12) United States Patent
Seidl

(10) Patent No.: US 10,512,737 B2
(45) Date of Patent: Dec. 24, 2019

(54) INHALATION DEVICE

(71) Applicant: PARI GmbH Spezialisten für effektive Inhalation, Starnberg (DE)

(72) Inventor: Christian Seidl, Munich (DE)

(73) Assignee: PARI GmbH Spezialisten für effektive Inhalation, Starnberg (DE)

( * ) Notice: Subject to any disclaimer, the term of this patent is extended or adjusted under 35 U.S.C. 154(b) by 242 days.

(21) Appl. No.: 15/469,659

(22) Filed: Mar. 27, 2017

(65) Prior Publication Data
US 2017/0281882 A1    Oct. 5, 2017

(30) Foreign Application Priority Data

Mar. 31, 2016   (EP) ..................................... 16163201

(51) Int. Cl.

| | |
|---|---|
| *A61M 11/02* | (2006.01) |
| *F04B 49/03* | (2006.01) |
| *A61M 16/00* | (2006.01) |
| *A61M 11/06* | (2006.01) |
| *A61M 16/20* | (2006.01) |
| *F04B 45/06* | (2006.01) |
| *F16K 17/164* | (2006.01) |
| *A61M 15/00* | (2006.01) |
| *F16K 15/14* | (2006.01) |

(52) U.S. Cl.
CPC .............. *A61M 11/02* (2013.01); *A61M 11/06* (2013.01); *A61M 15/0021* (2014.02); *A61M 16/0063* (2014.02); *A61M 16/0072* (2013.01); *A61M 16/208* (2013.01); *A61M 16/209* (2014.02); *F04B 45/06* (2013.01); *F04B 49/03* (2013.01); *F16K 15/145* (2013.01); *F16K 17/164* (2013.01); *A61M 2202/04* (2013.01); *A61M 2202/06* (2013.01)

(58) Field of Classification Search
CPC .............. A61M 11/02; A61M 15/0021; A61M 16/0063; A61M 16/209; A61M 16/208; F16K 17/164; F04B 49/03
See application file for complete search history.

(56) References Cited

U.S. PATENT DOCUMENTS 2,657,899 A    11/1953  Köhler et al.
4,300,593 A *  11/1981  Ritter .................... F16K 15/145
                                                          137/512.15

(Continued)

FOREIGN PATENT DOCUMENTS

| EP | 0 049 316 A1 | 4/1982 |
| EP | 0 170 715 B1 | 4/1988 |
| GB | 2 050 575 A  | 1/1981 |

OTHER PUBLICATIONS

European Examination Report and English language machine translation thereof dated Jun. 20, 2016 in connection with European Application No. 16163201.3.

*Primary Examiner* — Bradley J Osinski
(74) *Attorney, Agent, or Firm* — Wolf, Greenfield & Sacks, P.C.

(57) ABSTRACT

An inhalation device (1) comprising a compressor (2), an aerosol generator (3) and a pressure relief valve (4), wherein the compressor (2) is configured to provide a compressed gas for the aerosol generator (3) and the pressure relief valve (4) is configured to limit a pressure in the inhalation device (1).

9 Claims, 4 Drawing Sheets

(56) References Cited

U.S. PATENT DOCUMENTS

| | | | | |
|---|---|---|---|---|
| 4,932,313 A | * | 6/1990 | Gutknecht | F15B 15/1447 384/115 |
| 9,046,092 B2 | | 6/2015 | Boehm et al. | |
| 2007/0215150 A1 | * | 9/2007 | Boehm | A61M 11/06 128/203.12 |
| 2009/0286030 A1 | * | 11/2009 | Robert | A61L 2/18 428/36.91 |
| 2016/0067431 A1 | * | 3/2016 | Abate | A61M 11/005 128/200.16 |

* cited by examiner

INHALATION DEVICE

The invention relates to an inhalation device comprising a compressor and an aerosol generator.

Inhalation devices comprising a compressor and an aerosol generator are known in the prior art and are described, for example, in EP 0 170 715 B1.

EP 0 170 715 B1 describes a device for nebulising, distributing and mixing liquid and powdered substances by means of a compressed gas flow, in particular for the generation of aerosols for inhalation purposes. A compressor is specified as the compressed gas source, which produces a required overpressure or excess pressure (approximately 0.6 bar).

U.S. Pat. No. 9,046,092 B2 describes a compressor comprising two separate compression spaces.

The object of the present invention is to provide an improved inhalation device comprising a compressor and an aerosol generator.

This object is solved by an inhalation device comprising a compressor, an aerosol generator and a pressure relief valve, wherein the compressor is configured to provide a compressed gas for the aerosol generator and the pressure relief valve is configured to limit a pressure in the inhalation device.

Owing to the provision of the pressure relief valve, an optimum pressure for the aerosol generator can be provided—it is not necessary to select a lower pressure for reasons of safety. The occurrence of high pressures that could endanger a user or cause damage to the inhalation device can be prevented owing to the provision of the pressure relief valve. An aerosol with optimised properties, preferably a pressure of 1.0 to 2.0 bar, can thus be provided. An overpressure can lead to the end of a hose becoming detached from a hose connection. Since the pressure relief valve can prevent the occurrence of overpressures, the use of a pressure relief valve can make it possible to dispense with fastening devices, such as cable ties or hose clips, at that end of a hose that is connected to a hose connection.

An inhalation device is a device that is suitable for performing inhalation therapy.

The compressor is a fluid energy machine that is suitable for compressing gases. The compressor preferably comprises a rotary compressor, a screw compressor, a piston compressor, a swash plate compressor, a wobble piston compressor or a diaphragm compressor.

An aerosol generator preferably comprises a nebuliser, an atomiser, a humidifier, a compressed air nebuliser, an air atomiser, an electronic nebuliser, an electrohydrodynamic nebuliser, an electrostatic nebuliser, a nozzle nebuliser, a two-component nozzle or a combination thereof. In one embodiment, the aerosol generator is configured for use with ventilators.

Aerosols are mixtures of solid or liquid suspended particles and a gas. Aerosols are preferably provided for application on or in parts of the human or animal body such as the skin, body cavities, body orifices, the nose, the paranasal sinuses, the maxillary sinus, the frontal sinus, the sphenoidal sinus, the ethmoidal cells, the throat, the larynx, the trachea, the lungs, the stem bronchus, the bronchi, the bronchioles, the pulmonary alveoli, the joints or the abdominal cavity. Aerosols can be used to diagnose, prevent or treat diseases in humans and animals or to immunize humans or animals against diseases.

Pressure relief valves or safety valves are configured to prevent an unacceptable increase in pressure that can lead to the endangerment of a user or damage to a component. Pressure relief valves are configured to discharge fluids, gases, vapours or liquids from the pressurised region when an opening pressure is exceeded. In one embodiment, the pressure relief valve comprises a proportional valve, a full-lift safety valve, a standard safety valve, a spring-loaded safety valve, a weight-loaded safety valve, a medium-loaded safety valve, a direct-acting safety valve, a controlled safety valve or a combination thereof.

The compressed gas preferably comprises compressed air.

It is expedient to provide the pressure relief valve downstream of the compressor.

In one embodiment, the pressure relief valve is configured to limit a pressure inside the compressor, the aerosol generator or a hose. The hose is preferably configured to be able to guide compressed gas from the compressor to the aerosol generator. The pressure relief valve is expediently configured to offer mechanical protection to all components that are under pressure. The pressure relief valve can offer protection against a harmful pressure.

The pressure relief valve is preferably disposed adjacent to an outlet of the compressor. The compressor can thus be particularly well protected against overloading by too high a pressure.

In one embodiment, the pressure relief valve is provided on the hose or on the compressor. The pressure relief valve is preferably provided at an outlet of the compressor, adjacent to an end of the hose, or on a hose connection.

In one embodiment, a hose connection comprises a hose connection nozzle, an air connection nozzle, an air connection piece or a hose connection piece and is configured to be fixedly or detachably connected to an outlet of a compressor. It is preferable for the hose connection to have a circular cross-section. The hose connection can thus be easily combined with conventional hoses. The hose connection preferably comprises a plastic. It is particularly preferred for the hose connection to consist entirely of a plastic.

The compressor preferably comprises a piston. Owing to the combination with a pressure relief valve, a compressor comprising a piston can be configured such that the compressor has a particularly high degree of efficiency.

A compressor comprising a piston or piston compressor expediently operates according to the displacement principle. The compressor comprising a piston is preferably configured to encapsulate a gas in a volume, compress it and release it again. The compressor comprising a piston is preferably configured to compress a gas inside a cylinder by way of piston movement.

The piston is preferably a wobble piston. The compressor can thus be provided in a particularly simple manner.

In one embodiment, the wobble piston is rigidly connected with a connecting rod having an end which can be moved such that the wobble piston performs a lifting and rotating movement or a lifting and tilting movement. The movement of the end of the connecting rod is preferably a circular movement. The circular movement is expediently enabled by an eccentric connection of the end of the connecting rod to a shaft. The wobble piston is thereby expediently arranged in a cylinder.

In a preferred embodiment, a hose connection comprises a sealing surface in a front region, the hose or pressure hose sealing on said surface and preferably lying completely against said surface when an operating pressure is applied. In a preferred embodiment, an indentation, such as a notch or a groove, is made in a central region or central part of the hose connection such that an overpressure that is greater than the operating pressure can escape therethrough. The hose is preferably configured to inflate or distend in the case of overpressure, i.e. when there is an overpressure that is greater than the operating pressure, such that it is lifted off the sealing surface and the gas can pass from the hose into the groove. A toothing is preferably provided in the central region of the hose connection, which is configured to prevent the hose from sliding off or to hold the hose on the hose connection even in the case of overpressure.

In one embodiment, the hose has a circular or round cross-section. The hose expediently comprises a plastic. In one embodiment, the hose is made solely from plastic.

The hose connection preferably has an oval or elliptical cross-section, particularly preferred a circular or round cross-section.

In one embodiment, the hose connection is fixedly connected to the compressor. It is preferred for the hose connection to be fixedly connected to the hose.

A hose fastening device is preferably provided around the hose in the region of the indentation. The indentation can thereby be optimally sealed below the limiting pressure.

In one embodiment, the hose fastening device comprises a clamp, a cable tie or a hose clip. In one embodiment, a hose of an internal hosing is so short and the hose connections lie opposite one another with such a small offset that the hose remains fixed on the hose connections in the case of an overpressure. A hose fastening device, such as a clamp, a cable tie or a hose clip, is not provided.

An expansion is preferably provided on the hose connection. The hose can thus be connected in a particularly secure manner to the hose connection. The hose can be prevented from slipping off the hose connection.

The expansion is expediently configured such that it is suitable for pressing against the hose from the inside.

In one embodiment, the indentation extends through the expansion.

It is particularly expedient for the expansion to have an edge. The edge is preferably provided at the largest cross-section of the expansion. In one embodiment, the expansion is configured in the form of a toothing.

The compressor preferably includes a cylinder that comprises a plastic. The compressor can thus be produced in a particularly simple manner. The compressor preferably comprises a piston or a housing having a proportion of plastic or consisting of plastic. It is particularly preferred for the compressor to be produced mainly from one or more plastics. In one embodiment, the compressor comprises predominately non-metallic materials. In one embodiment, the cylinder does not comprise any metallic materials. In one embodiment, the piston does not comprise any metallic materials.

The compressor is preferably provided to generate an operating pressure of between 1 and 3 bar. The compressed gas is consequently particularly suitable for being supplied to the aerosol generator. It is particularly preferred for the pressure of the compressed gas to be between 1.0 and 2.0 bar when using the inhalation device. It is particularly expedient for the compressor to be configured to generate a degree of compression of between 1:2 and 1:20, preferably between 1:5 and 1:10, ideally of 1:8. The volumetric efficiency of the compressor can be influenced by the selection of the compression ratio.

An improved efficiency allows smaller or less expensive motors to be used for the compressor. A compressor with a higher degree of compression expediently generates higher dynamic pressures. In the event that a nozzle of the aerosol generator is blocked, the air outlet is kept closed or there is a kink in the hose, very high pressures, forces and temperatures can occur at components of the compressor, in the compressed air line and at the aerosol generator, which can lead to endangerment and damage. The hose can burst and a component, in particular a piston configured as a cup seal, can fall out. These problems can be prevented by using a pressure relief valve, and thus the efficiency of the compressor can be increased. A compressor having a high compression ratio and high pressures can be provided without running the risk that harmful overpressures will result if a nozzle of the aerosol generator is blocked or obstructed or if there is a kink in the hose, or running the risk that the compressor does not run, the power consumption of the compressor increases and the compressor heats up significantly. Defects of fuses can be prevented.

In one embodiment, a comparatively large suction cross-section is selected.

The object is also solved by a pressure relief valve for an inhalation device comprising a compressor and an aerosol generator, wherein the compressor is configured to provide a compressed gas for the aerosol generator and the pressure relief valve comprises a hose section and a hose connection, said hose connection having an indentation, said hose sealing the indentation below a limiting pressure in the interior of the hose and expanding above the limiting pressure in the interior of the hose such that the indentation is opened to the surroundings in order that gas can escape from the hose into the surroundings via the indentation.

In the following, the invention will be described in more detail by means of embodiment examples and with reference to the enclosed drawings. The drawings show the following:

Figure 1:
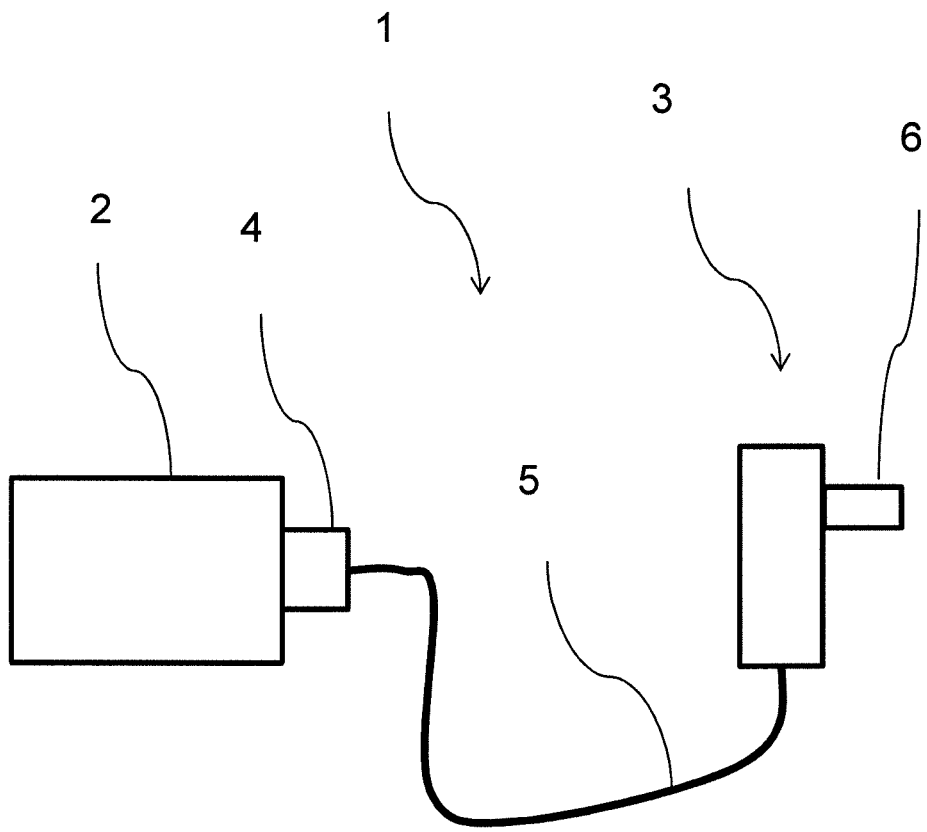
FIG. 1 shows a schematic diagram of an inhalation device comprising a compressor, an aerosol generator and a pressure relief valve.

FIG. 1 shows a schematic diagram of an inhalation device 1 comprising a wobble piston compressor 2, an aerosol generator 3 and a pressure relief valve 4. The pressure relief valve 4 is disposed on the wobble piston compressor 2. The aerosol generator 3 is a nozzle nebuliser 3 and is connected to the pressure relief valve 4 and the wobble piston compressor 2 via a compressed air line 5. A mouthpiece 6 is provided on the nozzle nebuliser 3.

When the inhalation device 1 is in use, the wobble piston compressor 2 generates compressed air that is guided to the nozzle nebuliser 3 via the compressed air line 5. With the aid of the compressed air and a liquid, the nozzle nebuliser 3 generates an aerosol. The aerosol can be inhaled by a user through the mouthpiece 6.

The pressure relief valve 4 limits the relative pressure between the inhalation device 1 and the surroundings to 10 bar.

If the relative pressure exceeds this value, the pressure relief valve 4 establishes a connection between the interior of the compressed air line 5 and the surroundings. Air can thereby escape out of the inhalation device 1 into the surroundings and the relative pressure in the inhalation device 1 decreases.

Endangerment of the user or persons in the vicinity and damage to the inhalation device 1 can thus be prevented. The compressor 2 can be configured to supply a high pressure. It is not necessary to configure the compressor 2 to supply a low pressure in order to prevent endangerment or damage. The inhalation device 1 can be configured such that it has a high degree of efficiency.

Figure 2:
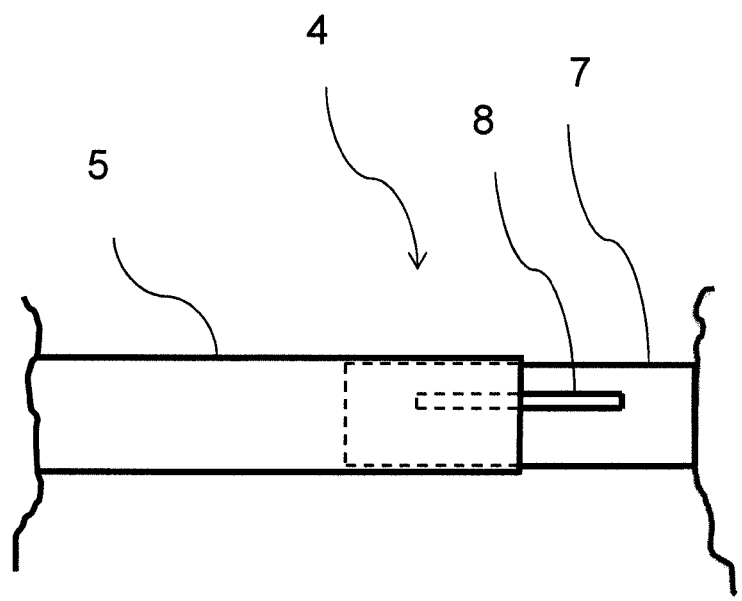
FIG. 2 shows a pressure relief valve.

FIG. 2 shows a pressure relief valve 4 such as can be used in an inhalation device 1, for example in the inhalation device 1 as shown in FIG. 1. The pressure relief valve 4 is shown in a state which it assumes in the presence of an operating pressure or in a pressureless state.

The pressure relief valve 4 comprises a hose connection nozzle 7, a groove 8 and one end of a hose 5. The hose connection nozzle 7 can be connected to a compressor 2. The hose 5 can be connected to a nebuliser 3. In the presence of an operating pressure or when the compressor 2 is switched off, the hose 5 lies flat on the hose connection nozzle 7. The interior of the hose 5 is sealed against the surroundings in such a manner that compressed air cannot escape from inside the hose 5 into the surroundings. The groove 8 is connected to the surroundings but not to the interior of the hose 5 or the hose connection nozzle 7.

Figure 3:
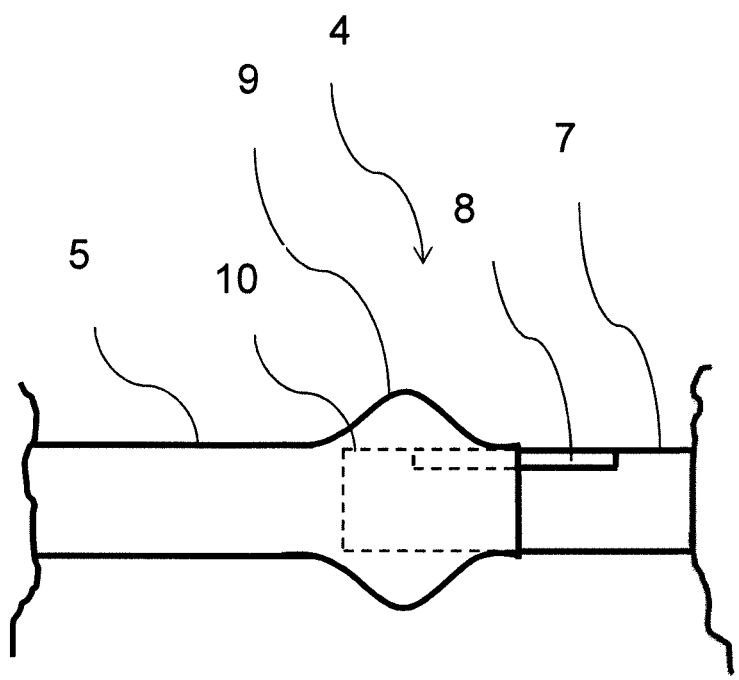
FIG. 3 shows the pressure relief valve as shown in FIG. 2 in the presence of a high pressure.

FIG. 3 shows the pressure relief valve 4 as shown in FIG. 2 in the presence of a high internal pressure or a pressure inside the hose 5 that exceeds a predetermined operating pressure. The relative pressure inside the hose 5 in relation to the surroundings is 3 bar.

Owing to the high relative pressure, the hose 5 is inflated such that it is lifted in part from the hose connection nozzle 7. This provides a connection between the interior of the hose 5 and the groove 8. Compressed air can escape from the interior of the hose 5, through the inflated area 9, past an outer side 10 of the hose connection nozzle 7 and into the surroundings via the groove 8. In this manner, a pressure inside the hose 5 can be reduced or a further increase in pressure can be prevented. The internal pressure is not able to lift the hose 5 from the hose connection nozzle 7 in the region on the outlet side of the groove 8 since the pressure is sufficiently reduced following creation of a passage out of the interior of the hose 5 into the groove 8. The hose 5 therefore does not slip from the hose connection nozzle 7 even in the event of a high relative pressure.

When the internal pressure decreases and an intended relative pressure is achieved, the pressure relief valve 4 reassumes the state as shown in FIG. 2. Compressed air can no longer escape through the groove 8 into the surroundings.

Figure 4:
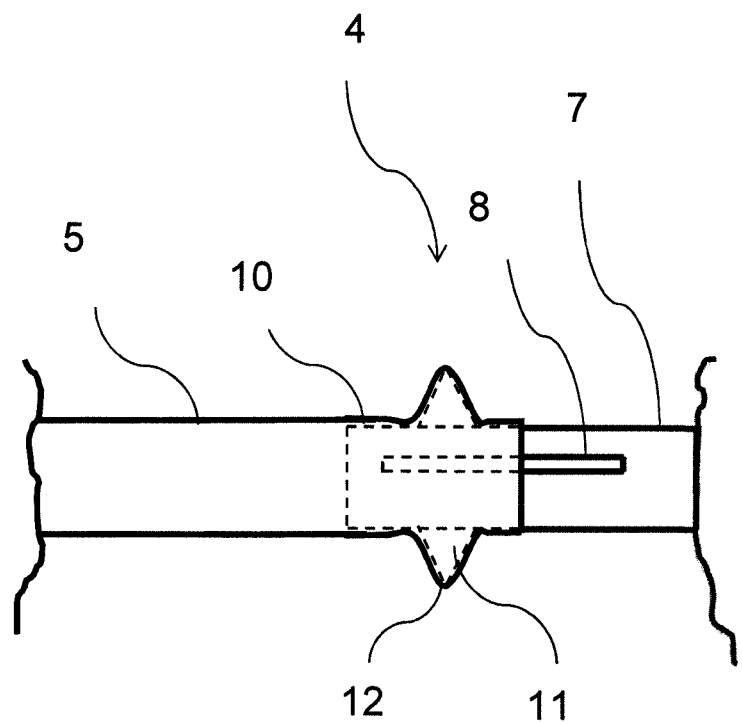
FIG. 4 shows a pressure relief valve comprising a retaining edge.

FIG. 4 shows a pressure relief valve 4 comprising a retaining edge 11. The pressure relief valve 4 is configured in accordance with the pressure relief valve 4 as shown in FIGS. 2 and 3. The retaining edge 11 is provided in order to better prevent the hose 5 from slipping off the hose connection nozzle 7. The retaining edge 11 is a region of the hose connection nozzle 7 that has a larger diameter than the regions of the hose connection nozzle 7 that are adjacent in the longitudinal direction. At the location with the largest diameter, the retaining edge 11 comprises a sharp edge 12.

In the presence of an operating pressure or in the pressureless state, the hose 5 lies tightly against the retaining edge 11. As a result, the connection between the hose 5 and the retaining edge 11 is particularly strong.

Figure 5:
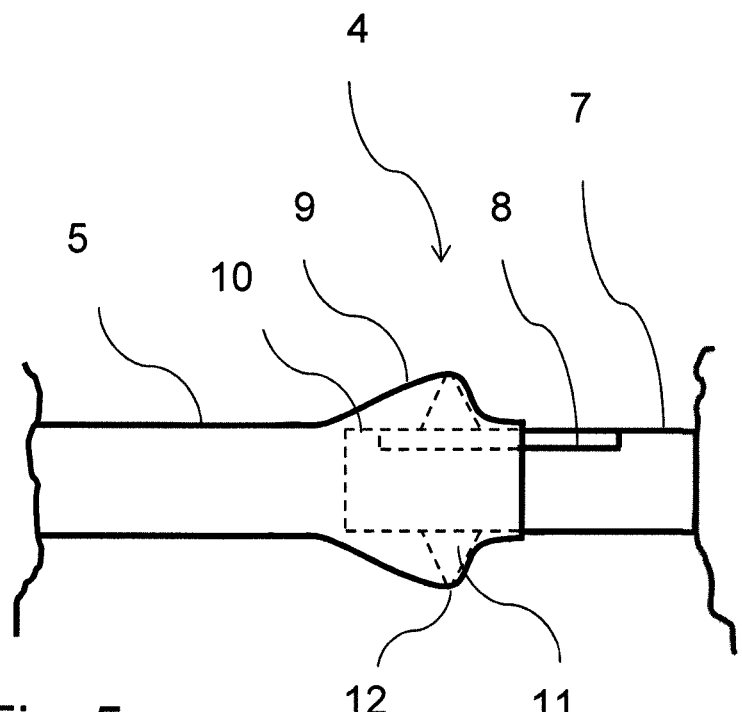
FIG. 5 shows the pressure relief valve as shown in FIG. 4 in the presence of a high pressure.

FIG. 5 shows the pressure relief valve 4 as shown in FIG. 4 in the presence of a high pressure in the interior of the hose 5. As is the case in the pressure relief valve 4 as shown in FIG. 3, an inflated area 9 is formed such that compressed air can escape from the interior of the hose 5, through the inflated area 9, past an outer side 10 of the hose connection nozzle 7 and into the surroundings via the groove 8. The retaining edge 11 prevents the hose 5 from slipping off. The retaining edge 11 defines the area in which the hose 5 can inflate. The hose 5 can inflate on the pressure side, or effectively the side of the retaining edge that faces the compressor 2. The region of the hose 5 that is located on the side of the retaining edge 11 which faces the adjacent end of the hose 5 lies flat on the retaining edge 11 and the hose connection nozzle 7.

Figure 6:
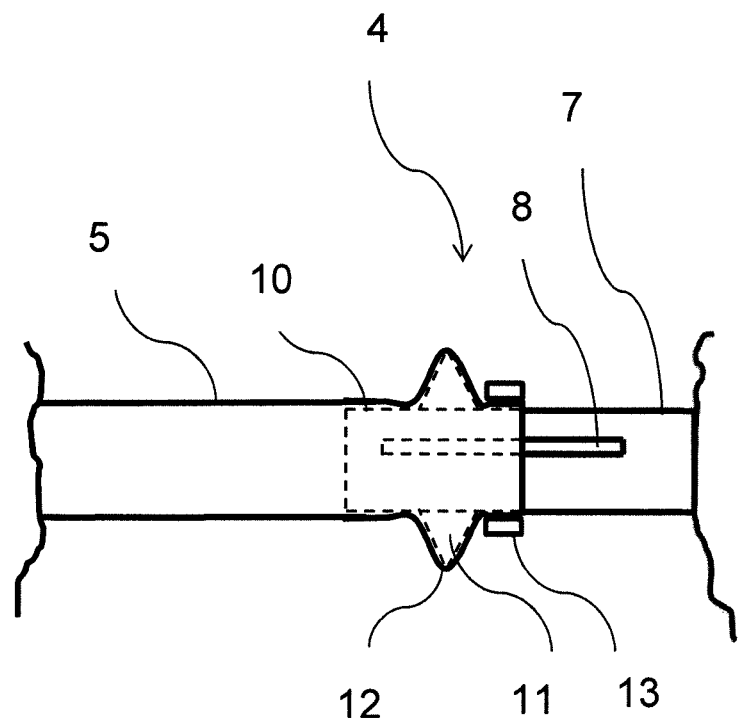
FIG. 6 shows a pressure relief valve comprising a retaining edge and a clip.

FIG. 6 shows a pressure relief valve 4 comprising a retaining edge 11 and a hose clamp 13 in the pressureless state. The pressure relief valve 4 shown in FIG. 6 corresponds to the pressure relief valve 4 as shown in FIGS. 4 and 5, with the exception that a hose clamp 13 is provided. The hose clamp 13 constitutes an additional protection against slipping off of the hose 5. It is provided adjacent to the retaining edge 11 on the side of the retaining edge 11 which faces the adjacent end of the hose 5. The hose clamp 13 extends around the hose 5 and the hose connection nozzle 7. The hose clamp 13 is provided in a region of the hose connection nozzle 7, through which the groove 8 extends.

Figure 7:
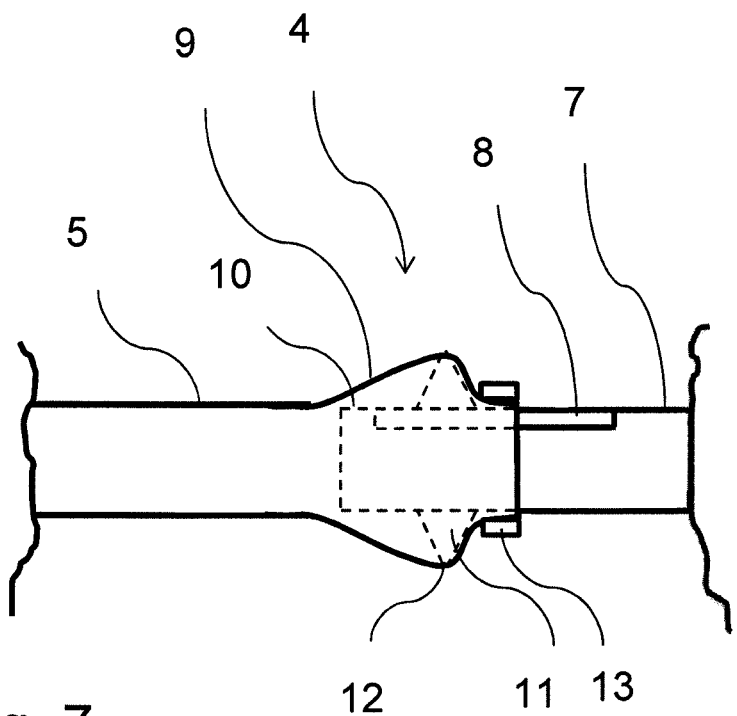
FIG. 7 shows the pressure relief valve as shown in FIG. 6 in the presence of a high pressure.

FIG. 7 shows the pressure relief valve 4 as shown in FIG. 6 in the presence of a high pressure. The hose clamp 13 can prevent the hose from slipping off. It can furthermore prevent the passage from becoming larger, owing to the inflation of the hose 5, than provided by the cross-section of the groove 8.

LIST OF REFERENCE NUMBERS

1 Inhalation device
2 Compressor
3 Aerosol generator
4 Pressure relief valve
5 Hose
6 Mouthpiece
7 Hose connection nozzle
8 Groove
9 Inflated region
10 Outer side of the hose connection nozzle
11 Retaining edge
12 Sharp edge
13 Hose clamp

The invention claimed is:

1. An inhalation device comprising a compressor, an aerosol generator and a pressure relief valve, wherein the compressor is configured to provide a compressed gas for the aerosol generator and the pressure relief valve is configured to limit a pressure in the inhalation device, wherein the pressure relief valve comprises a hose section and an indentation in a hose connection nozzle, said hose section being part of a hose that connects the aerosol generator and the compressor, said hose section sealing the indentation below a limiting pressure in the interior of the hose section and expanding above the limiting pressure in the interior of the hose section such that the indentation is opened to a surrounding area in order that gas can escape from the hose section into the surrounding area via the indentation and wherein the indentation comprises a lengthwise groove in the hose connection nozzle and wherein the hose section partially overlaps the lengthwise groove.

2. The inhalation device according to claim 1, wherein the pressure relief valve is disposed adjacent to an outlet of the compressor.

3. The inhalation device according to claim 1, wherein the compressor comprises a piston.

4. The inhalation device according to claim 3, wherein the piston is a wobble piston.

5. The inhalation device according to claim 1, wherein in the region of the indentation, a hose fastening device is provided around the hose section.

6. The inhalation device according to claim 1, wherein an expansion is provided on the hose connection nozzle.

7. The inhalation device according to claim 1, wherein the compressor includes a cylinder that comprises a plastic.

8. The inhalation device according to claim 1, wherein the compressor generates an operating pressure of between 1 and 3 bar.

9. The inhalation device according to claim 1, wherein the pressure relief valve is disposed in line with the hose.

* * * * *